United States Patent
Liu et al.

(10) Patent No.: US 10,004,404 B2
(45) Date of Patent: Jun. 26, 2018

(54) PORTABLE VEIN PROJECTOR

(71) Applicant: Zhejiang University, Hangzhou (CN)

(72) Inventors: Huafeng Liu, Hangzhou (CN); Shining Ma, Hangzhou (CN)

(73) Assignee: ZHEJIANG UNIVERSITY, Hangzhou (CN)

(*) Notice: Subject to any disclaimer, the term of this patent is extended or adjusted under 35 U.S.C. 154(b) by 173 days.

(21) Appl. No.: 15/140,522

(22) Filed: Apr. 28, 2016

(65) Prior Publication Data
US 2016/0317036 A1   Nov. 3, 2016

(30) Foreign Application Priority Data
Apr. 29, 2015 (CN) .......................... 2015 1 0212656

(51) Int. Cl.
| | |
|---|---|
| H04N 7/18 | (2006.01) |
| A61B 5/00 | (2006.01) |
| H04N 5/225 | (2006.01) |
| H04N 5/33 | (2006.01) |
| H04N 5/232 | (2006.01) |
| H04N 9/31 | (2006.01) |
| A61B 5/02 | (2006.01) |
| A61B 90/00 | (2016.01) |

(52) U.S. Cl.
CPC ............ *A61B 5/0079* (2013.01); *A61B 5/489* (2013.01); *H04N 5/2256* (2013.01); *H04N 5/23229* (2013.01); *H04N 5/33* (2013.01); *H04N 9/3179* (2013.01); *H04N 9/3194* (2013.01); *A61B 5/0075* (2013.01); *A61B 5/02007* (2013.01); *A61B 2090/366* (2016.02)

(58) Field of Classification Search
CPC ..................................................... A61B 5/0079
USPC ........................................................... 348/77
See application file for complete search history.

(56) References Cited

U.S. PATENT DOCUMENTS

| | | | | |
|---|---|---|---|---|
| 9,736,402 | B2* | 8/2017 | De Bruijn | H04N 5/332 |
| 9,789,267 | B2* | 10/2017 | Wood | A61M 5/427 |
| 2005/0264702 | A1* | 12/2005 | Yoshii | G09G 3/3406 |
| | | | | 348/687 |
| 2010/0201895 | A1* | 8/2010 | Golub | A61B 5/0059 |
| | | | | 348/759 |
| 2011/0125028 | A1* | 5/2011 | Wood | A61B 5/0064 |
| | | | | 600/476 |

(Continued)

*Primary Examiner* — Leron Beck
(74) *Attorney, Agent, or Firm* — Matthias Scholl, PC; Matthias Scholl

(57) ABSTRACT

A portable vein projector, including an LED light source, a CMOS image sensor, a semi-transparent and semi-reflecting mirror, a micro-projector, and an image processing unit. The LED light source operates to project near-infrared light on the skin surface area. The near-infrared light is reflected by the skin surface, and part of reflected light penetrates through the semi-transparent and semi-reflecting mirror, enters into the CMOS image sensor to form an image in the CMOS image sensor. The image is transmitted from the CMOS image sensor to the image processing unit where the image is processed, and the image is transmitted to the micro-projector. The micro-projector outputs visible light. The visible light is reflected by the semi-transparent and semi-reflecting mirror and is imaged on the skin surface area to yield a vein image.

6 Claims, 6 Drawing Sheets

(56) References Cited

U.S. PATENT DOCUMENTS

| | | | |
|---|---|---|---|
| 2014/0313556 A1* | 10/2014 | Liu | G02B 27/0103 359/13 |
| 2015/0002647 A1* | 1/2015 | Qian | H04N 5/33 348/77 |
| 2016/0128627 A1* | 5/2016 | Demos | A61B 5/0075 600/473 |

* cited by examiner

PORTABLE VEIN PROJECTOR

CROSS-REFERENCE TO RELATED APPLICATIONS

Pursuant to 35 U.S.C. § 119 and the Paris Convention Treaty, this application claims the foreign priority benefit of Chinese Patent Application No. 201510212656.4 filed Apr. 29, 2015, the contents of which, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, and Cambridge, Mass. 02142.

BACKGROUND OF THE INVENTION

Field of the Invention

The invention relates to a medical device, and in particular, to a portable vein projector.

Description of the Related Art

Conventional vein projectors are expensive to produce, bulky, and non-portable.

SUMMARY OF THE INVENTION

In view of the above-described problems, it is one objective of the invention to provide a portable vein projector that is inexpensive to produce, small in size, and convenient for carrying. The portable vein projector has good imaging quality and is suitable for mass production.

To achieve the above objective, in accordance with one embodiment of the invention, there is provided a portable vein projector, comprising an LED light source, a CMOS image sensor, a semi-transparent and semi-reflecting mirror, a micro-projector, and an image processing unit. The LED light source operates to project near-infrared light on a skin surface area. The near-infrared light is reflected by the skin surface, and part of reflected light penetrates through the semi-transparent and semi-reflecting mirror, enters into the CMOS image sensor to form an image in the CMOS image sensor. The image is transmitted from the CMOS image sensor to the image processing unit where the image is processed, and the image is transmitted to the micro-projector adapted to output visible light. The visible light is reflected by the semi-transparent and semi-reflecting mirror and is imaged on the skin surface area to yield a vein image.

In a class of this embodiment, the near-infrared light projected by the LED light source on the skin surface area has a peak wavelength of 850 nm, so that the produced image has an optimal contrast.

Because the LED light source is approximately considered as a Lambert reflector, of which lights have the brightness varying from different directions, and light energy is unevenly distributed. To solve the problem, a scatter plate is disposed in front of the LED light source to achieve a better imaging and a uniform light distribution in different directions.

When the LED light source is bright, the scattering intensity of the fat on the vein surface is strengthened, meanwhile the contrast of the vein to the fat surrounding the vein is weakened; when the LED light source is not bright, few light reaches the vein, the contrast of the vein to the fat is also weakened. Therefore, the LED light source is connected to a driver module. The driver module operates to control a drive current of the LED light source, so that the LED light source projects the near-infrared light having a light intensity of 0.11 cd/m$^2$, enabling the vein to be the clearest.

In a class of this embodiment, the CMOS image sensor is disposed vertically over the skin surface area. The semi-transparent and semi-reflecting mirror is disposed between the CMOS image sensor and the skin surface area, and is inclined at 45 degrees. The micro-projector is disposed on a left side or a right side of the semi-transparent and semi-reflecting mirror. As a result, the optical axis of projection is completely coincident with the optical axis of imaging, and the position and the size of the projected image are completely corresponding to the skin surface area.

In a class of this embodiment, the image processing unit comprises:

an image processing module, operating to mirror the image transmitted from the CMOS image sensor to the image processing unit;

a grey preprocessing module, operating to average grey values of pixel points in a vein area in the image processed by the image processing module, then substrate a resulting average from each of the grey values of the pixel points to achieve the grey preprocessing;

a denoising module, operating to eliminate Gaussian noise and salt and pepper noise in the image after grey preprocessing based on a grey K-Nearest Neighbor (KNN) Algorithm; and a contrast enhancing module, operating to enhance a contrast of the image after denoising using a threshold segmentation method so as to highlight the vein area; the threshold segmentation method sets a grey threshold, and places pixel points having higher grey values than the grey threshold into one class, and pixel points having lower grey values than the grey threshold into another class.

In a class of this embodiment, the image processing module further comprises an image sharpening module. The image sharpening module sharpens edges of the image after contrast enhancement using a Laplace operator, enabling edges of the vein to be clear.

Advantages of the portable vein projector according to embodiments of the invention are summarized as follows:

1) The projector features low cost, small size, high accuracy, high contrast and convenient operation.

2) The projector employs the semi-transparent and semi-reflecting mirror so that the near-infrared light is able to transmit through the mirror, and the visible light is reflected, eliminating adverse influences brought by stray lights.

3) The projector is designed in line with the phenomenon that hemoglobins and subcutaneous tissues in the vein have different near-infrared absorption bands, thus the projector can be universally applied to superficial vein detection.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a portable vein projector are described below. It should be noted that the following examples are intended to describe and not to limit the invention.

Figure 1:
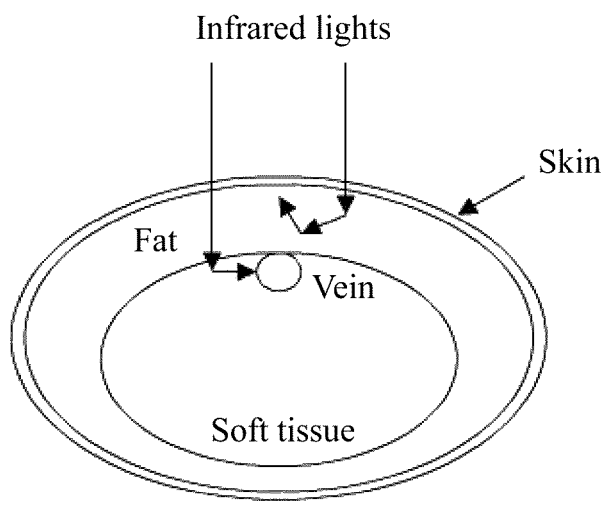
FIG. 1 is a diagram showing infrared optical properties of different tissues of human being.

As shown in FIG. 1, the design principle of the portable vein projector is that the vein and tissues surrounding the vein have different absorptions and reflections for infrared lights: the fat scatters and rarely absorbs the infrared lights; because hemoglobins exist in vein blood, the vein has stronger absorption for infrared lights than other subcutaneous tissues. The skin thickness ranges from 0.5 to 4 mm, and the average thickness is 2 mm. When a far-infrared radiation is employed (above 3 μm), most of the far-infrared radiation can only acts on the shallow surface or on the dermis, and only a small part of the far-infrared radiation is able to permeate into the skin; when the near-infrared radiation is employed, the penetration depth of the near-infrared radiation is about 1 cm while the penetration depth of the far-infrared radiation is only between 0.05 and 1 mm.

Figure 2:
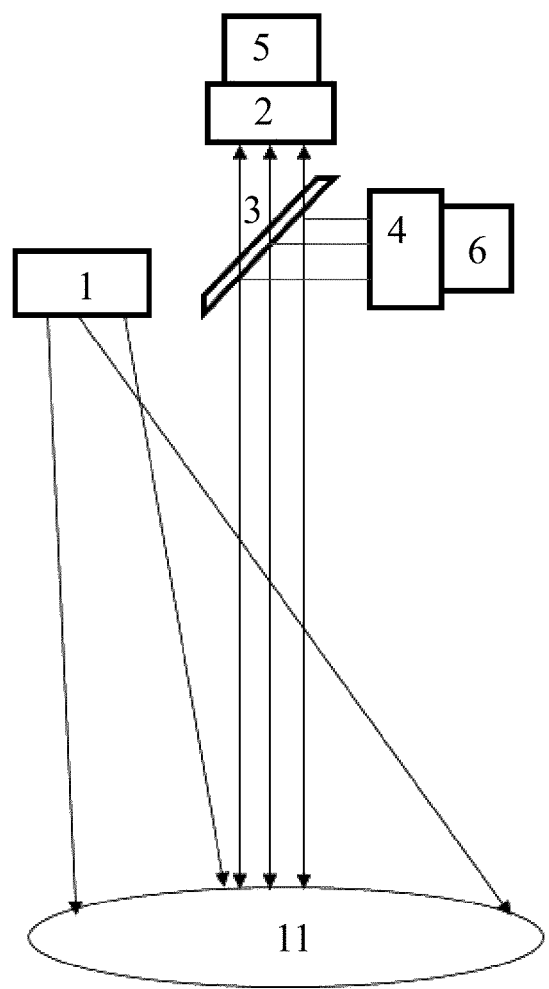
FIG. 2 is a diagram showing an optical design of a portable vein projector in accordance with one embodiment of the invention.
Figure 3:
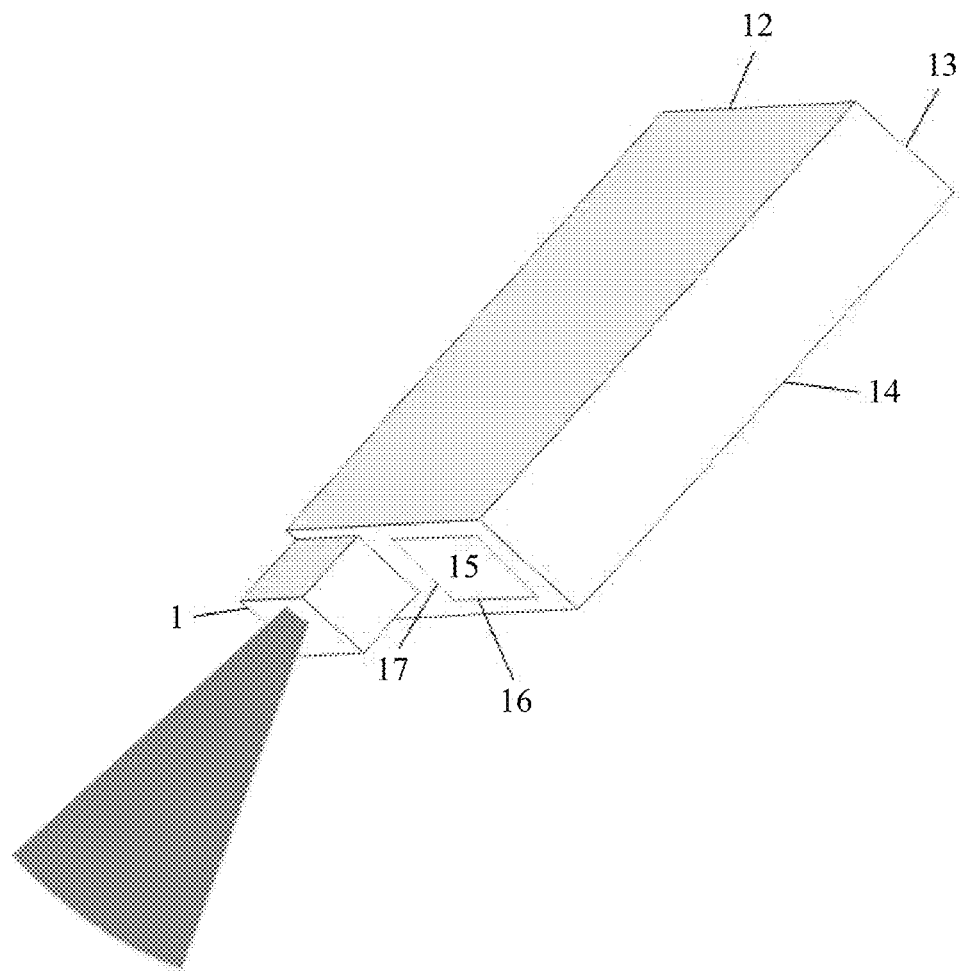
FIG. 3 is a diagram showing a package structure of a portable vein projector in accordance with one embodiment of the invention.
Figure 6:
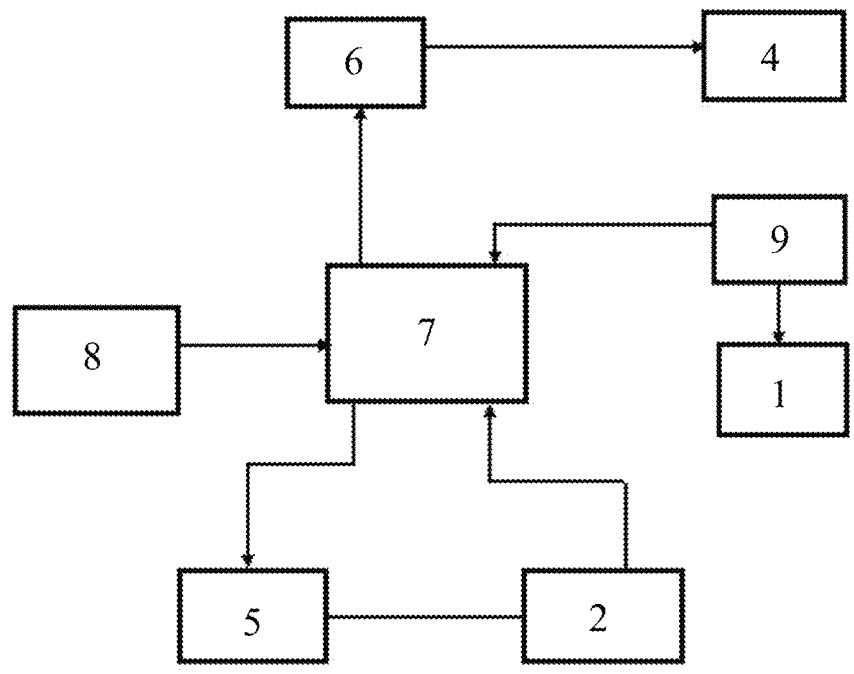
FIG. 6 is a diagram showing a connection between modules of a portable vein projector in accordance with one embodiment of the invention.

According to the design principle, as shown in FIGS. 2, 3, and 6, the portable vein projector comprises an LED light source 1, a CMOS camera 2, a semi-transparent and semi-reflecting mirror 3, a micro-projector 4, a CMOS driving module 5, a projector driving module 5, an ARM core controlling module 7, an image processing module 8, and a power supply module 9.

The CMOS driving module 5 is integrated on the CMOS camera 2. The projector driving module 6 is integrated on the micro-projector. The image processing module 8 and the power supply module 9 are integrated and are disposed on one circuit board, and an ARM core controlling module 7 is adapted to control the read-in, the processing, and the read-out of the data flow. A battery connected to the circuit board operates to supply power for a projector system. The CMOS camera 2 and the micro-projector 4 are connected to a circuit via a respective interface, and the power supply module operates to supply power. FIG. 6 shows a relationship between modules and the data transmission of the projector system.

The LED light source 1 projects near-infrared light on the back of the hand 11, and the back of the hand scatters the near-infrared light, one part of which penetrates through the semi-transparent and semi-reflecting mirror 3 and enters into the CMOS camera 2, and another part carrying information of the back of the hand cannot transmit through the semi-transparent and semi-reflecting mirror 3. The CMOS camera 2 transmits a collected real-time image to the ARM core controlling module 7, and the image processing module 8 of the core controlling module 7 sharpens the collected image. The image is then transmitted to the micro-processor 4, and the micro-processor outputs visible light which is unable to transmit through the semi-transparent and semi-reflecting mirror 3 and is reflected and projected on a corresponding position on the back of the hand, thus the vein is imaged.

Figure 4:
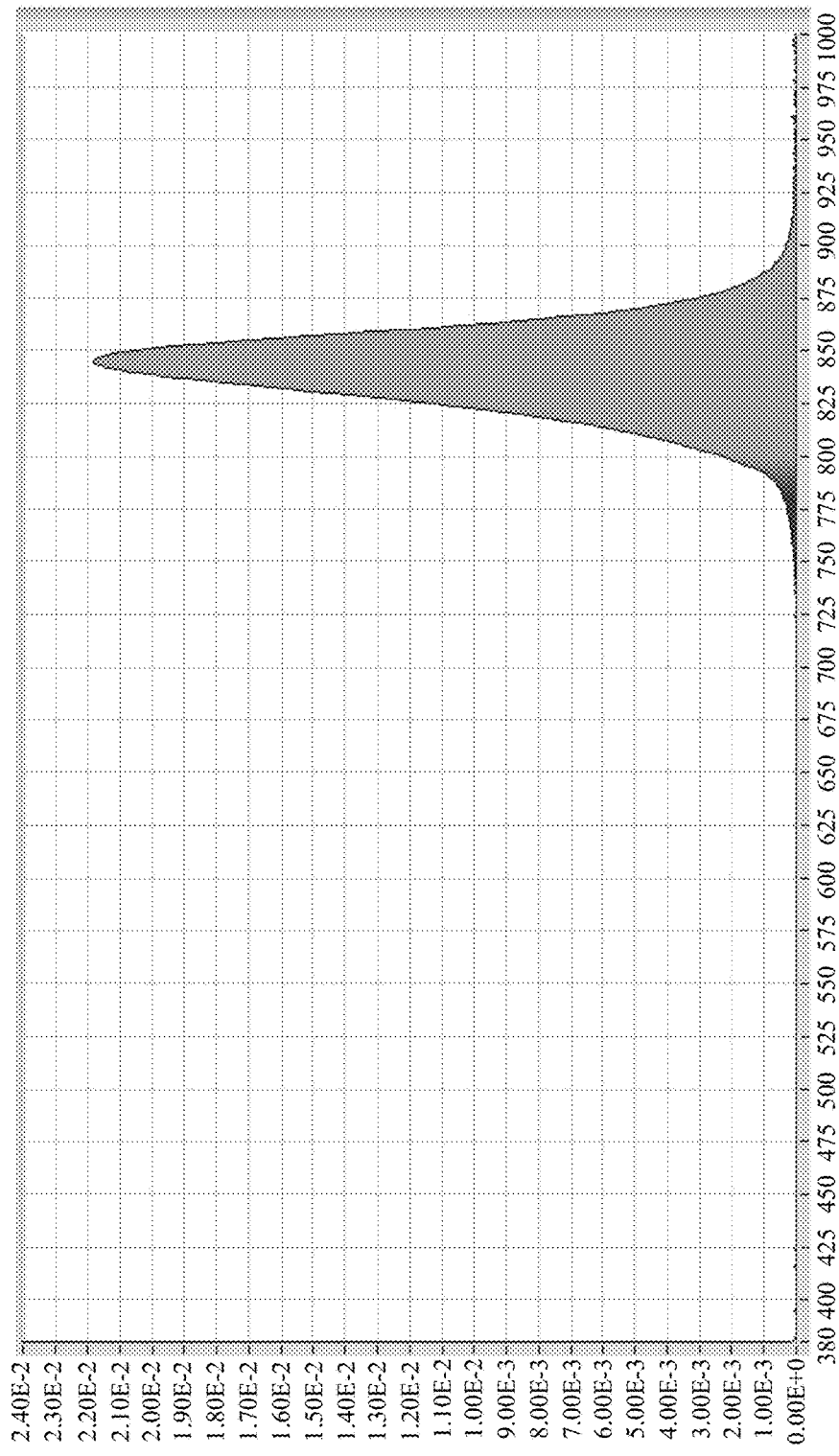
FIG. 4 is a diagram showing a spectral power distribution of an LED light source of a portable vein projector in accordance with one embodiment of the invention.

Steps for using the portable vein projector are as follows:

1) The near-infrared light is projected on the back of the hand 11, and is imaged in the CMOS camera 2; the image is displayed on a computer. Parameters of the LED light source 1 are adjusted so as to produce an imaging condition having an optimal contrast. Human body absorbs infrared radiation, and an absorption is determined by a wave length of the infrared radiation and a condition of human skin; according to the principle of matched absorption, when the wave length of the infrared radiation is corresponding to an absorption wavelength of an irradiated object, the object produces a resonance absorption, and when the infrared radiation perfectly matches with the absorption wavelength of the irradiated object, an optimal absorption is realized. Therefore, the wavelength range of the light source is required to be first adjusted: after testing LED light sources having three different wavelengths, the infrared light having a wavelength of 850 nm is proved to produce the clearest vein image, thus the LED light source having the wavelength of 850 nm is taken as the light source of the projector system, and the spectral power distribution diagram is shown in FIG. 4.

Figure 5A:
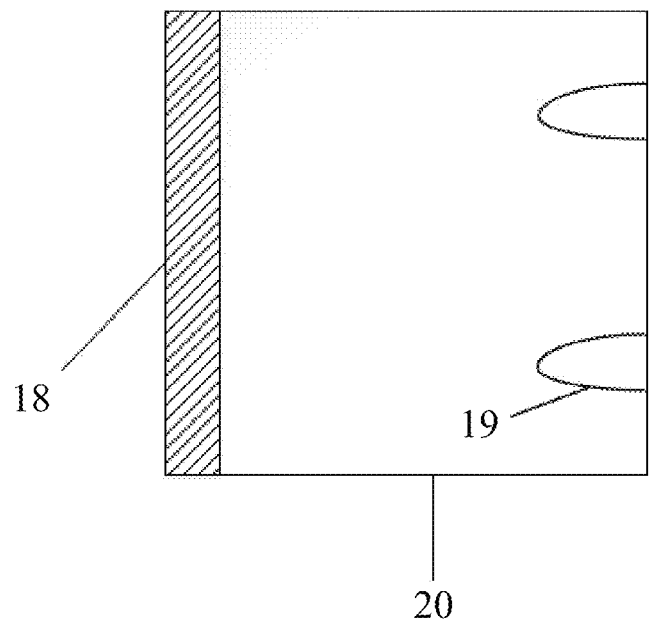
FIG. 5A is a side view of an LED light source of a portable vein projector in accordance with one embodiment of the invention.
Figure 5B:
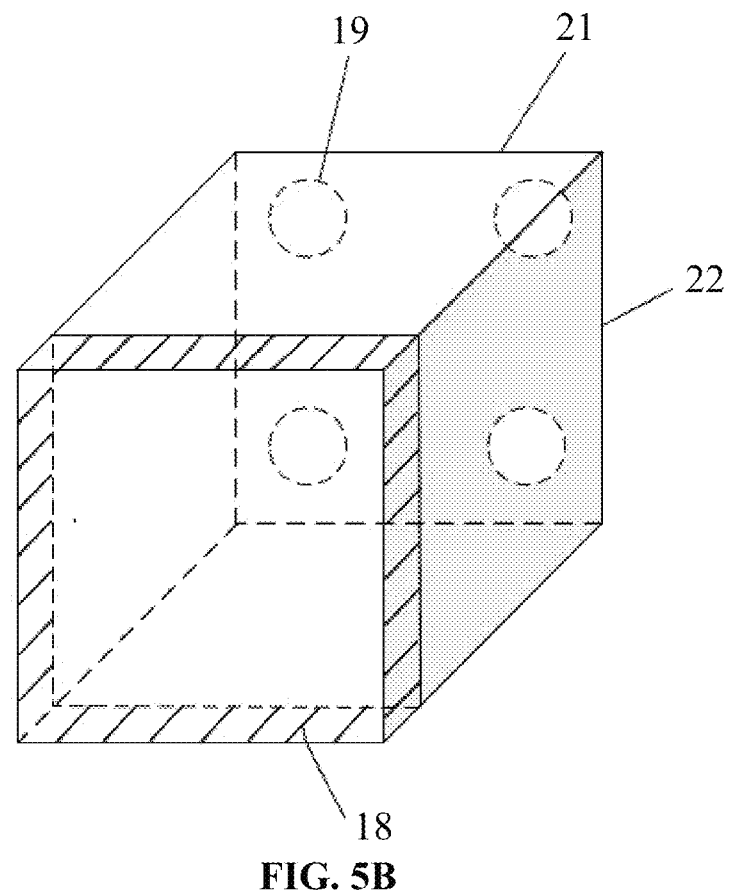
FIG. 5B is a front view of an LED light source of a portable vein projector in accordance with one embodiment of the invention.

Then, an optical field distribution of the light source is adjusted: because the LED light source is approximately considered as a Lambert reflector, of which lights have the brightness varying from different directions, and light energy is unevenly distributed. To solve the problem, a scatter plate 18 is disposed in front of the LED light source to achieve a better imaging and an equal light distribution in different directions, as shown in FIGS. 5A-5B. FIG. 5A is a side view of the LED light source, in which a first side 20 of the LED light source is a distance from the scatter plate 18 to a fixed surface and is about 6 cm in practice. FIG. 5B is a front view of the LED light source, where 2*2 arrayed LED lights are distributed on a 5*5 cm² rectangular surface. The scatter plate 18 is rectangular-shaped, and a length of a second side 21 of the LED light source is 4 cm, a length of a third side 22 of the LED light source is 4 cm.

At last, a drive current of the LED light source is adjusted: when the LED light source is bright, a scattering intensity of the fat on the vein surface is strengthened, meanwhile the contrast of the vein to the fat surrounding the vein is weakened; when the LED light source is not bright, few light reaches the vein, the contrast of the vein to the fat is also weakened. Therefore, the LED light source is required to have a practicable light intensity, and a light intensity of 0.11 cd/m² after scattering is proved by tests to produce a clearest vein image.

2) As shown in FIG. 2, an optical system enabling an optical path of image collection and an optical path of projection to completely coincide is provided. The position and size of the projected image completely match with the corresponding skin surface area. First, the position of the image is required to match with the skin surface area, which means that the optical path of image collection and the optical path of projection are required to completely coincide. The projector employs the semi-transparent and semi-reflecting mirror 3 so that the near-infrared light is able to transmit through the mirror, and the visible light is reflected. The semi-transparent and semi-reflecting mirror 3 is disposed in optical paths so as to ensure that the optical paths coincide, and that the CMOS camera 2 only receives the near-infrared light, eliminating adverse influences brought by stray lights and so on. It is worth mentioning that the optical axis of image collection of the CMOS camera 2 and the optical axis of projection of the micro-projector are required to intersect at a central part of the semi-transparent and semi-reflecting mirror 3, and the semi-transparent and semi-reflecting mirror 3 is inclined at 45 degrees, so that the optical axis of projection is completely coincident with the optical axis of imaging.

Then the size of the projected image is required to completely match with the corresponding skin surface area, thus a field of view of the image collected by the CMOS camera 2 is required to be coincident with a field of view of the image projected on the corresponding skin surface area. Meanwhile, the image collected by the CMOS camera 2 is ensured to completely transmit through the semi-transparent and semi-reflecting mirror 3, and lights projected by the micro-projector 4 are ensured to be completely reflected by the semi-transparent and semi-reflecting mirror 3, which means that the semi-transparent and semi-reflecting mirror 3 could not limit fields of view. In the example, a project angle of view of the micro-projector 4 is 36 degrees (horizontal) *22 degrees (vertical), and the project angle of view doesn't change when the micro-projector is redesigned and an imaging optical system is added thereto. Distances from the micro-processor 4 to the CMOS camera 2 and to the semi-transparent and semi-reflecting mirror 3 are required to be as short as possible, so that a loss of image information is avoided and a utilization rate of light energy is improved. In the example, a distance from a center of the micro-projector 4 to a center of the semi-transparent and semi-reflecting mirror 3 is 1.3 cm, and a distance from a center of the CMOS camera 2 to the center of the semi-transparent and semi-reflecting mirror 3 is also 1.3 cm. For the reason of space saving, the semi-transparent and semi-reflecting mirror 3 is designed to have an elliptical shape, a length of a long axis is 2.54 cm, and a length of a short axis is 1.2 cm.

Figure 7:
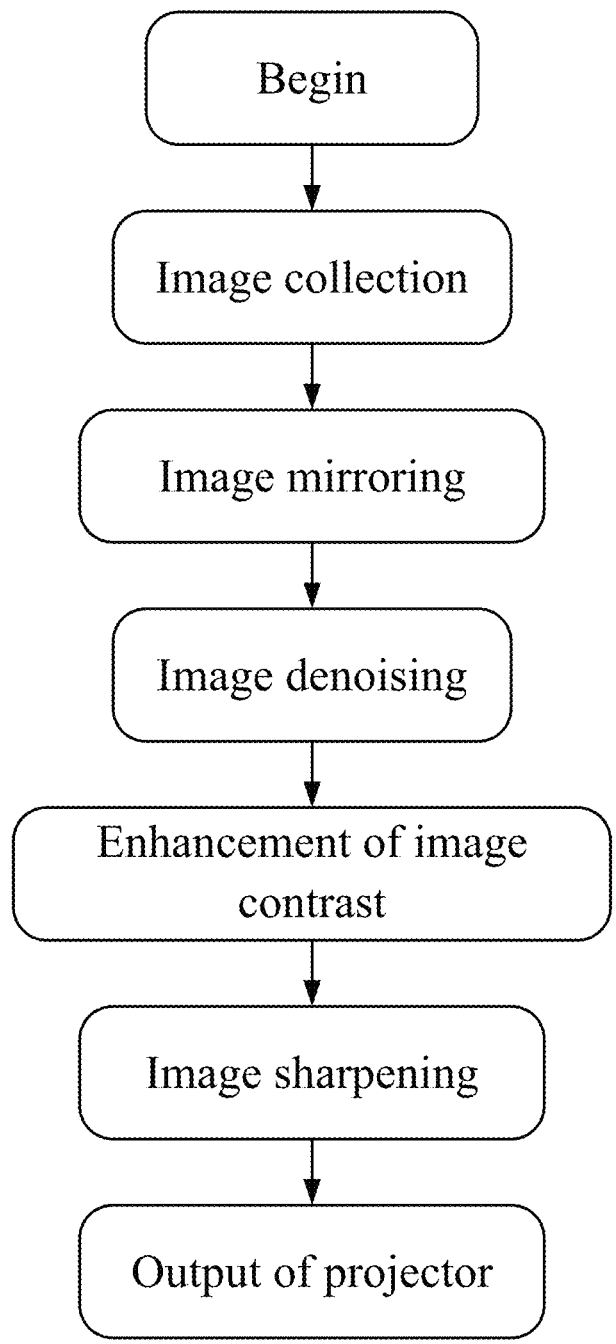
FIG. 7 is a flow chart of an image processing unit of a portable vein projector in accordance with one embodiment of the invention.

3) The image processing module 8 sharpens the image, improves the contrast and enables the vein image to be clear. Because the LED light source is not bright, the overall grey value of the image is low, thus as shown in FIG. 7, the contrast of the image is improved and a vein edge is sharpened.

Because the lights projected by the micro-projector 4 are reflected by the semi-transparent and semi-reflecting mirror 3, thus the image collected by the CMOS camera 2 is a mirror image of the image projected by the micro-projector, thus first the image collected by the CMOS camera 2 needs mirroring, then grey values of a vein area are collected and averaged, and grey values of all pixel points of the image minus a mean, eliminating adverse impact brought by scattered lights of the fat. The image is then denoised. Based on a grey KNN (K-Nearest Neighbor) Algorithm, Gaussian noise and salt and pepper noise in the image are eliminated, which means using an average grey value of K-Nearest Neighbors of a central pixel point in a window as a substitute for a grey value of the central pixel point.

Finally, the contrast of the image is enhanced using a threshold segmentation method: the threshold segmentation method sets a grey threshold, and pixel points having higher grey values than the grey threshold is set as the highest, and pixel points having lower grey values than the grey threshold is set as the lowest, enabling the vein image to be clear.

Meanwhile, the image is sharpened using a difference operator. In the example, the vein edge is sharpened using a Laplace operator, enabling the vein edge to be clear and ensuring edge pixels are in a dark area or a bright area of the image:

$$H = \begin{bmatrix} -1 & -1 & -1 \\ -1 & 9 & -1 \\ -1 & -1 & -1 \end{bmatrix}$$

An ideal image is generated by combining the two methods.

4) After testing, the projector system is encapsulated, and positions of all elements are fixed. A cuboid box is sleeved on the projector system, having a volume of 12 cm*25 cm*5 cm, similar to a remote controller. As shown in FIG. 3, a length of a fourth side 12 of the cuboid box is 12 cm, a length of a fifth side 13 of the cuboid box is 5 cm, and a length of a sixth side 14 of the cuboid box is 25 cm. The cuboid box employs lighttight plastic material; positions of all elements are strictly fixed according to design requirements, a focal length of the micro-projector is also fixed, so that the projector system has a clearest imaging position. According to an angle of view of the CMOS camera 2, a distance for optimal imaging of the example is 30 cm, and deviation of the distance can only affect imaging quality, a position of the vein image is not affected, either, ratio of the vein to the vein image being 1:1 is not affected. In use, the distance meets the requirements of doctors, and is easy to use.

A forefront end of the projector system is provided with two holes. The first hole is adapted to install the LED lights source 1, comprising an LED light 19 and the scatter plate 18. Certain distance is needed between the scatter plate 18 and the LED light 19, thus the light source protrudes from the cuboid box of the projector system, ensuring an even distribution of lights projected by the projector. The second hole is sheathed with a transparent plastic film 15 featuring high transmittance, on the one hand, a surface of the semi-transparent and semi-reflecting mirror 3 is prevented from pollution, on the other hand, the projector system is provided with a light transmitting hole so as to guarantee that lights emitted by the projector are not stopped and transmit through the light transmitting hole. An area of the plastic film 15 is 4 cm*4 cm, a length of a seventh side 16 of the plastic film 15 is 4 cm, and a length of an eighth side 17 of the plastic film 15 is also 4 cm.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A portable vein projector, comprising:
   an LED light source;
   a CMOS image sensor;
   a semi-transparent and semi-reflecting mirror;
   a micro-projector; and
   an image processing unit;
   wherein:
   in use, the LED light source projects near-infrared light on a skin surface area; the near-infrared light is reflected by the skin surface area, and part of reflected light penetrates through the semi-transparent and semi-reflecting mirror, enters into the CMOS image sensor to form an image in the CMOS image sensor; the image is transmitted from the CMOS image sensor to the image processing unit where the image is processed, and processed image is transmitted to the micro-projector; the micro-projector outputs visible light the visible light is reflected by the semi-transparent and semi-reflecting mirror and is imaged on the skin surface area to yield a vein image; and the image processing unit comprises:
an image processing module;
a grey preprocessing module;
a denoising module; and
a contrast enhancing module;
wherein
the image processing module operates to mirror the image transmitted from the CMOS image sensor to the image processing unit;
the grey preprocessing module operates to average grey values of pixel points in a vein area in the image processed by the image processing module, then substrate a resulting average from each of the grey values of the pixel points to achieve the grey preprocessing;
the denoising module operates to eliminate Gaussian noise and salt and pepper noise in the image after grey preprocessing based on a grey K-Nearest Neighbor (KNN) Algorithm; and
the contrast enhancing module operates to enhance a contrast of the image after denoising using a threshold segmentation method so as to highlight the vein area; the threshold segmentation method sets a grey threshold, and places pixel points having higher grey values than the grey threshold into one class, and pixel points having lower grey values than the grey threshold into another class.

2. The projector of claim 1, wherein the near-infrared light projected by the LED light source on the skin surface area has a peak wavelength of 850 nm.

3. The projector of claim 1, wherein a scatter plate is disposed in front of the LED light source.

4. The projector of claim 1, wherein a driver module is connected to the LED light source; the driver module operates to control a drive current of the LED light source, so that the LED light source projects the near-infrared light having a light intensity of 0.11 cd/m$^2$.

5. The projector of claim 1, wherein the CMOS image sensor is disposed vertically over the skin surface area; the semi-transparent and semi-reflecting mirror is disposed between the CMOS image sensor and the skin surface area, and is inclined at 45 degrees; the micro-projector is disposed on a left side or a right side of the semi-transparent and semi-reflecting mirror.

6. The projector of claim 1, wherein the image processing module further comprises an image sharpening module; the image sharpening module sharpens edges of the image after contrast enhancement using a Laplace operator.

* * * * *